(12) United States Patent
Verkaik et al.

(10) Patent No.: US 11,759,114 B2
(45) Date of Patent: Sep. 19, 2023

(54) EXTRAVASCULAR CUFF WITH DISPLACEABLE LATERAL RESTRAINT

(71) Applicants: RTM Vital Signs LLC, Philadelphia, PA (US); Thomas Jefferson University, Philadelphia, PA (US)

(72) Inventors: Josiah Verkaik, Boise, ID (US); Jeffrey I Joseph, Penn Valley, PA (US)

(73) Assignees: RTM Vital Signs LLC, Philadelphia, PA (US); Thomas Jefferson University, Philadelphia, PA (US)

( * ) Notice: Subject to any disclaimer, the term of this patent is extended or adjusted under 35 U.S.C. 154(b) by 307 days.

(21) Appl. No.: 17/338,812

(22) Filed: Jun. 4, 2021

(65) Prior Publication Data

US 2021/0378524 A1 Dec. 9, 2021

Related U.S. Application Data

(60) Provisional application No. 63/034,645, filed on Jun. 4, 2020.

(51) Int. Cl.
*A61B 5/0215* (2006.01)
*A61B 5/022* (2006.01)
*A61B 5/00* (2006.01)

(52) U.S. Cl.
CPC ........ *A61B 5/0215* (2013.01); *A61B 5/02241* (2013.01); *A61B 5/6876* (2013.01); *A61B 2562/028* (2013.01); *A61B 2562/0247* (2013.01); *A61B 2562/168* (2013.01)

(58) Field of Classification Search
CPC ............ A61B 2562/0247; A61B 5/686; A61B 5/6876; A61B 2562/168; A61B 5/0215; A61B 5/02241; A61B 2562/028; A61B 5/02141
See application file for complete search history.

(56) References Cited

U.S. PATENT DOCUMENTS

| 4,398,542 A | 8/1983 | Cunningham et al. |
| 4,592,747 A | 6/1986 | Pool |
| 4,825,876 A | 5/1989 | Beard |
| 4,881,939 A | 11/1989 | Newman |

(Continued)

FOREIGN PATENT DOCUMENTS

JP          H03112534 A    5/1991

*Primary Examiner* — Eric F Winakur
*Assistant Examiner* — Emily C Clement
(74) *Attorney, Agent, or Firm* — Christopher & Weisberg, P.A.

(57) ABSTRACT

An implantable extravascular pressure sensing system includes a cuff including a first brace portion affixed to a second brace portion and defining a longitudinal axis therebetween. The first brace portion defines a fluid chamber, the fluid chamber defining a recessed aperture. A first lateral restraint and a second lateral restraint are disposed between the first brace and the second brace, the first lateral restraint and the second lateral restraint being configured to be displaceable in a direction orthogonal to the longitudinal axis. A diaphragm is coupled to the fluid chamber and sealing the recessed aperture. A fluid is disposed within the fluid chamber for exhibiting a hydraulic pressure in communication with the diaphragm. A pressure sensor is coupled to the first brace portion, the pressure sensor being configured to measure a change in the hydraulic pressure when a force is imparted on the diaphragm.

18 Claims, 8 Drawing Sheets

(56) References Cited

U.S. PATENT DOCUMENTS

| | | | |
|---|---|---|---|
| 4,920,972 | A | 5/1990 | Frank et al. |
| 5,044,203 | A | 9/1991 | Wiest et al. |
| 5,722,414 | A | 3/1998 | Archibald et al. |
| 6,221,024 | B1 | 4/2001 | Miesel |
| 7,389,134 | B1 | 6/2008 | Karicherla et al. |
| 8,360,984 | B2 | 1/2013 | Yadav et al. |
| 8,491,518 | B2 | 7/2013 | Schnell et al. |
| 2003/0097073 | A1 | 5/2003 | Bullister et al. |
| 2009/0270740 | A1 | 10/2009 | Keilman et al. |
| 2011/0066046 | A1 | 3/2011 | Young et al. |
| 2015/0133796 | A1 | 5/2015 | Yadav |
| 2015/0289772 | A1 | 10/2015 | Huang et al. |
| 2019/0365249 | A1 | 12/2019 | Verkaik et al. |

EXTRAVASCULAR CUFF WITH DISPLACEABLE LATERAL RESTRAINT

CROSS-REFERENCE TO RELATED APPLICATION

This application is related to and claims priority to U.S. Provisional Patent Application Ser. No. 63/034,645, filed on Jun. 4, 2020, entitled EXTRAVASCULAR CUFF WITH DISPLACEABLE LATERAL RESTRAINT, the entirety of which is incorporated herein by reference.

TECHNICAL FIELD

The present application relates generally to blood pressure sensors, and, more particularly, to an implantable extravascular blood pressure system, an implantable extravascular cuff, and attachment element adapted to couple the cuff to a blood vessel.

BACKGROUND

A patient's vital signs provide information useful for detecting and/or monitoring medical conditions. Known devices for measuring vital signs include, for example, blood pressure cuffs which attach to a patient's upper arm, pulse oximeters designed to be placed around the patient's fingertip, thermometers for measuring body temperature, stethoscopes for observing biological sounds, and tonometers designed to measure pressure. Although often used to measure pressure inside of an eye, tonometers may also be implanted within a patient to measure blood pressure in the arteries and veins. One or more existing tonometers use a discrete force sensing element known to severely deform the blood vessel during applanation, i.e., flattening caused by the application of pressure. Other types of pressure sensors may be implanted within a blood vessel wall. However, such pressure sensors typically necessitate the presence of significant hardware inside the blood vessel that may be hazardous for the patient including blood flow obstructions and the potential for thrombus formation. Thus, an extravascular pressure sensor that does not breach the vessel wall has fewer safety risks as compared to a more-invasive extravascular tonometer.

The concept of applanation, as it relates to the blood vessel under Laplace's law, dictates that when a pressure sensor causes a blood vessel wall to applanate, the pressure measured inside the pressure sensor will be approximately equal to the pressure measured inside the blood vessel. Contact pressure value generated by applanation depends on the position and level of flattening. However, rigid tonometers performing applanation may generate internal blood vessel wall stress that may compromise the vessel over time and cause measurement errors. Under high stress conditions the tissue may remodel and become thinner in constrained low stress areas and thicker in areas of higher stress where acute bending is imposed on the vessel in regions of high curvature. In addition, rigid tonometers may be prone to errors associated with the size, shape, and position of the tonometer's pressure sensor with respect to the blood vessel on account of not having a means to allow the vessel to expand to facilitate dilation or a pulsatile pressure load.

SUMMARY

Some embodiments advantageously provide a system for an implantable extravascular pressure sensing system.

In one aspect, the implantable extravascular pressure sensing system includes a cuff including a first brace portion affixed to a second brace portion and defining a longitudinal axis therebetween. The first brace portion defines a fluid chamber, the fluid chamber defining a recessed aperture. A first lateral restraint and a second lateral restraint are disposed between the first brace and the second brace, the first lateral restraint and the second lateral restraint being configured to be displaceable in a direction orthogonal to the longitudinal axis. A diaphragm is coupled to the fluid chamber and sealing the recessed aperture. A fluid is disposed within the fluid chamber for exhibiting a hydraulic pressure in communication with the diaphragm. A pressure sensor is coupled to the first brace portion, the pressure sensor being configured to measure a change in the hydraulic pressure when a force is imparted on the diaphragm.

In another aspect, the system further includes a first bracket and a second bracket. The first bracket and the second bracket are each disposed on opposite sides of the pressure sensor and are configured to affix the first brace portion to the second brace portion.

In another aspect, the first lateral restraint is at least partially disposed within the first bracket and the second lateral restraint is at least partially disposed with the second bracket.

In another aspect, the first bracket and the second bracket each include a first plurality of apertures, and the first lateral restraint and the second lateral restraint each include a first plurality of protuberances sized and configured to be displaceable into and out of the first plurality of apertures.

In another aspect, the first plurality of protuberances extends away from each of a respective one of the first lateral restraint and the second lateral restraint in a direction orthogonal to the longitudinal axis.

In another aspect, the first lateral restraint and the second lateral restraint each define a bore there through.

In another aspect, the first lateral restraint and the second lateral restraint are pliable.

In another aspect, the first lateral restraint and the second lateral restraint are configured to contour a blood vessel restrained between them.

In another aspect, the first lateral restraint and the second lateral restraint each include a blood vessel contact portion and a first plurality of protuberances spaced a distance from the blood vessel contact portion.

In another aspect, the first plurality of protuberances are separated from the blood vessel contact portion by a necked portion.

In yet another aspect, the implantable extravascular pressure sensing system includes a cuff including a first brace portion affixed to a second brace portion at a fixed distance and defining a longitudinal axis and a blood vessel receiving volume therebetween. The first brace portion defines a fluid chamber. The fluid chamber defines a recessed aperture. A first lateral restraint and a second lateral restraint are disposed between the first brace and the second brace. The first lateral restraint and the second lateral restraint are pliable and are configured to be displaceable in a direction orthogonal to the longitudinal axis and to substantially enclose the blood vessel receiving volume. A diaphragm is coupled to the fluid chamber and seals the recessed aperture. A fluid is disposed within the fluid chamber for exhibiting a hydraulic pressure in communication with the diaphragm. A pressure sensor is coupled to the first brace portion, the pressure sensor is configured to measure a change in the hydraulic pressure when a force is imparted on the diaphragm.

In another aspect, the system further includes further including a first bracket and a second bracket. The first bracket and the second bracket are disposed on opposite sides of the pressure sensor and are configured to affix the first brace portion to the second brace portion.

In another aspect, the first lateral restraint is at least partially disposed within the first bracket and the second lateral restraint is at least partially disposed with the second bracket.

In another aspect, the first bracket and the second bracket each include a first plurality of apertures, and the first lateral restraint and the second lateral restraint each include a first plurality of protuberances sized and configured to be displaceable into and out of the first plurality of apertures.

In another aspect, the first plurality of protuberances extends away from each of a respective one of the first lateral restraint and the second lateral restraint in a direction orthogonal to the longitudinal axis.

In another aspect, the first lateral restraint and the second lateral restraint each define a bore there through.

In another aspect, the first lateral restraint and the second lateral restraint are at least partially composed of silicone.

In another aspect, the first lateral restraint and the second lateral restraint each include a blood vessel contact portion and a first plurality of protuberances spaced a distance from the blood vessel contact portion.

In another aspect, the first plurality of protuberances are separated from the blood vessel contact portion by a necked portion.

In yet another aspect, the implantable extravascular pressure sensing system includes a cuff including a first brace portion affixed to a second brace portion and defining a longitudinal axis and a blood vessel receiving volume therebetween. The first brace portion defines a fluid chamber. The fluid chamber defining a recessed aperture. A first lateral restraint and a second lateral restraint are disposed between the first brace and the second brace. The first lateral restraint and the second lateral restraint are each pliable and are configured to be displaceable in a direction orthogonal to the longitudinal axis and to substantially enclose the blood vessel receiving volume. A first bracket and a second bracket are disposed on opposite sides of the pressure sensor and are configured to affix the first brace portion to the second brace portion. The first lateral restraint and the second lateral restraint each include a first portion configured to contact a blood vessel when a blood vessel is disposed within the blood vessel receiving volume and a bore extending through the first portion. A second portion is spaced a distance from the first portion by a necked portion. The second portion is configured to move within a portion of the respective one of the first bracket and the second bracket. A diaphragm is coupled to the fluid chamber and seals the recessed aperture. A fluid is disposed within the fluid chamber for exhibiting a hydraulic pressure in communication with the diaphragm. A pressure sensor is coupled to the first brace portion. The pressure sensor is configured to measure a change in the hydraulic pressure when a force is imparted on the diaphragm.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 6 is another axial sectional view of the cuff shown in FIG. 3 at lead-in;

DETAILED DESCRIPTION

Before describing in detail exemplary embodiments, it is noted that the embodiments reside primarily in combinations of apparatus components related to an extravascular cuff with lateral restraints. Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Some embodiments include an extravascular cuff constructed in accordance with the principles of the present invention configured to measure blood pressure from a blood vessel disposed within the cuff. The pressure sensing system includes a diaphragm and a hydraulic fluid. Further details of the extravascular cuff and pressure sensing system are disclosed in U.S. Patent Publication No. 2019/0365249, the entirety of which is expressly incorporated herein by reference.

Referring now to the drawings in which like reference designators refer to like elements there is shown in FIGS. 1-8 an exemplary implantable extravascular pressure sensing system generally designated as "10." The system 10 includes an implantable extravascular cuff with displaceable lateral restraints. The implantable extravascular cuff may be referred to herein as a brace or "the cuff 12" and is configured to be implanted within a patient, such as a human or animal patient. Upon implantation, the cuff 12 at least partially surrounds a blood vessel 14 (as shown in FIGS. 3-6), to measure blood pressure and/or perform additional or alternative medical diagnostics. The cuff 12 may surround select portions of the blood vessel 14 without necessitating the complete encircling of the blood vessel 14 or the cuff 12 may surround at least a portion of the blood vessel 14.

Referring now to FIGS. 1-4, in one configuration, the cuff 12 includes a first brace portion 16, a second brace portion 18 opposite the first brace portion 16, and a longitudinal axis 20 defined therebetween. The first brace portion 16 and the second brace portion 18 may be rigidly affixed to each other at a fixed distance. The cuff 12 also includes a first bracket 22 and a second bracket 24 coupling the first brace portion to the second brace portion 18. The first brace portion 16 may include a rigid housing 26 having a main body 28 including a proximal region 30 configured to receive an electronic communication assembly 32 and a distal region 34 opposite the proximal region 30. The proximal region 30 and the distal region 34 may define a housing axis (not shown) extending therethrough. Similarly, the second brace portion 18 may include a rigid housing 36 having a main body 38 including a proximal region 40 and a distal region 42 opposite the proximal region 40. The proximal region 40 and the distal region 42 defining a housing axis (not shown) extending therethrough. In one configuration, the first brace portion 16 may house various electronics, such as a pressure sensor 44 (as shown in FIG. 5), whereas the second brace portion 18 may serve as an attachment element or lock to secure the cuff 12 to the blood vessel 14. The pressure sensor 44 may be located within the first brace portion 16 such that it is disposed between the first bracket 22 and the second bracket 24. In other words, the first bracket 22 and the second bracket 24 may be disposed on opposite sides of the pressure sensor 44. In other configurations, the first brace portion 16 and/or the second brace portion 18 may house various medical diagnostic components.

The housing 26 of the first brace portion 16 and the housing 36 of the second brace portion 18 may be made of a titanium material or another biocompatible material having a low density, relatively high strength, and relatively high level of corrosion resistance. The housing 36 of the second brace portion 18 may have the same or similar dimensions as the dimensions of the housing 26 of the first brace portion 16. The first and second brackets 22, 24 may also be made of a titanium material or another biocompatible material having a low density, relatively high strength, and a relatively high level of corrosion resistance. The first and second brackets 22, 24 may also be configured to assist the cuff 12 in accommodating blood vessels of varying size and adjust for dilation and constriction of the blood vessel 14 while maintaining mechanical coupling of an outer surface of a diaphragm 46 with a wall of the blood vessel 14 in applanation when the cuff 12 is used a blood pressure sensor. Further, when the diaphragm 46 is contact with the blood vessel 14, the pressure sensor 44 is configured to measure a change in the hydraulic pressure when a force is imparted on the diaphragm 46.

Figure 1:
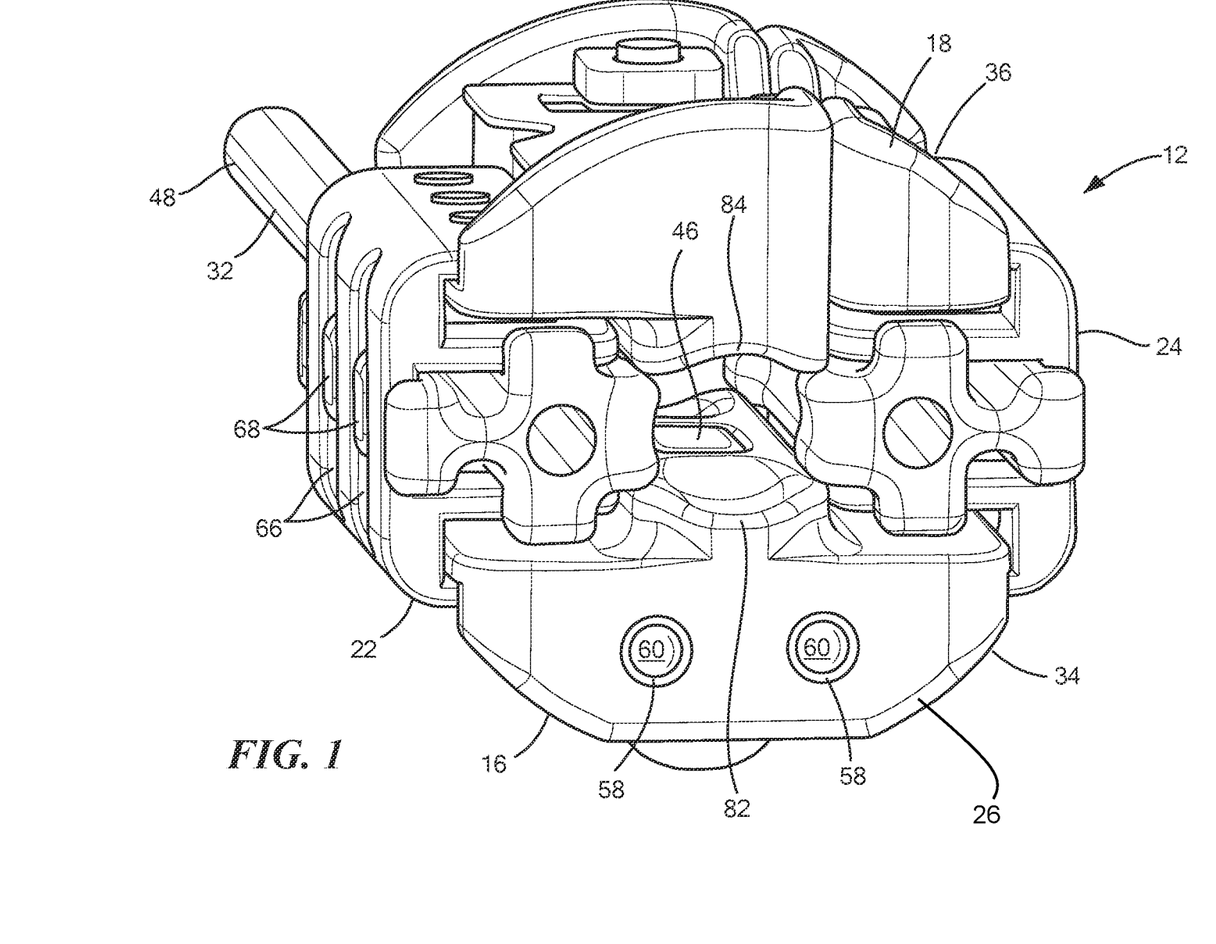
FIG. 1 is an assembled view of an exemplary extravascular cuff with lateral restraints.
Figure 2:
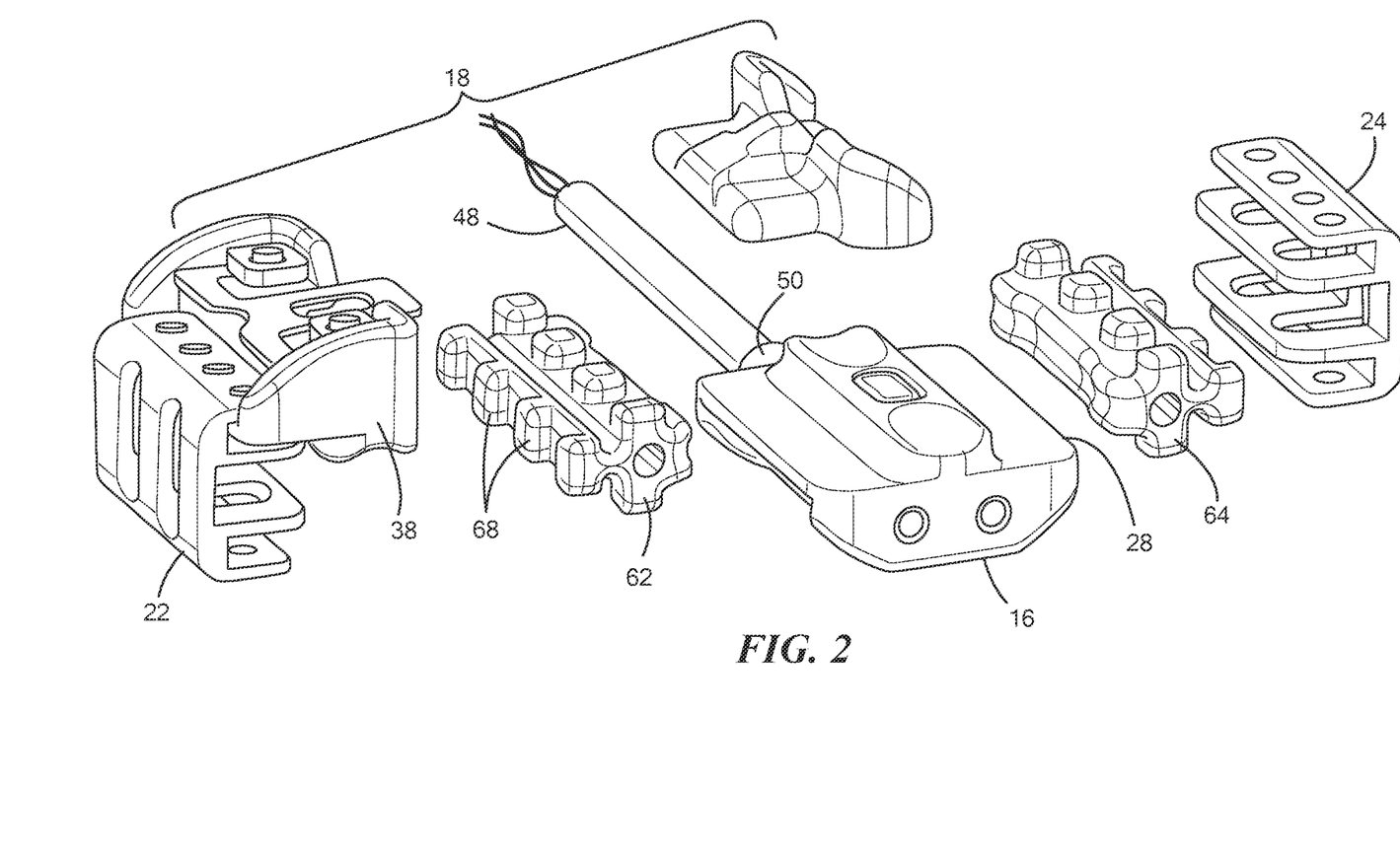
FIG. 2 is a disassembled view of the cuff shown in FIG. 1.

As shown in FIG. 2, the electronics communication assembly 32, which is configured to couple to the proximal region 30 of the first brace portion 16, may include an electric cable 48 and a semi-flexible sleeve 50. For example, the electric cable 48 may be flexible and may include a covering surrounding one or more electric wires (not shown) extending throughout the covering which establish communication between electronics that may be disposed within the first brace portion 16 and at least one of a power source, a controller, and a processor (not shown) external to or implanted within the patient. The electric cable 48 may have a diameter between 0.5 to 1.5 mm, such as 1.0 mm. The sleeve 50 surrounds a portion of the electric cable 48 at an interface between the proximal region 30 of the housing 26 and the electric cable 48. The sleeve 50 provides bend relief for the electric cable 48 to prevent unwanted stress while maintaining flexibility. As such, the sleeve 50 may be solvent bonded to the outer surface of electric cable 48 with the sleeve 50 being optionally interlocked in epoxy when coupling to the housing 26. The sleeve 50 may be made of a material such as, without limitation, polyurethane, and may include a length between 2.0 mm to 4.0 mm, such as 3.0 mm, and a diameter between 1.5 mm to 2.5 mm, such as 2.0 mm.

Although not described in detail herein, the proximal region 30 of the housing 26 may include an electronic feedthrough assembly coupled thereto for providing a leak-tight passage of electrical conductors to the electronic communication assembly 32. For example, the electronic feedthrough assembly may include a flange laser welded to the housing 26, an insulator, e.g., a ceramic insulator, coupled to the flange, and one or more wires extending through the flange for coupling to the wires of the electric cable 48. A cover is coupled to the housing 26 to cover the wires and electronics within the housing 26. In one configuration, the cover is made from the same material as the housing 26, such as titanium, for providing a leak-tight enclosure. The cover may also be made from an alternative material that is biocompatible and otherwise suitable for implantation, as is known to a person of ordinary skill in the art of implantable devices.

Referring now to FIG. 5, the first brace portion 16 defines a fluid chamber 52 which further defines a recessed aperture 54 which is sealed by a diaphragm 46. A fluid, such as silicone fluid, may be disposed within the fluid chamber 52 for exhibiting a hydraulic pressure consistent with the pressure applied to the diaphragm 46, such as an inner surface of the diaphragm 46 from the blood vessel 14. Hydraulic generally refers to fluid in a confined space (closed system) wherein the fluid is a medium to transmit force. This is in accordance with the discovery of Pascal that a pressure applied to any part of a confided fluid transmits to every other part with no loss. The pressure acts with equal force on all equal areas of the confining walls in a direction perpendicular to the wall surfaces. The pressure sensor 44 is coupled to the first brace portion 16 and is configured to measure a change in the hydraulic pressure when the force is imparted on the diaphragm 46, such as on an outer surface of the diaphragm 46. As such, the diaphragm 46 may be a compliant diaphragm configured to be secured, i.e., mechanically coupled, against a wall of the blood vessel 14 to facilitate transduction of the blood pressure through a wall of the blood vessel 14.

In one configuration, the hydraulic pressure within the diaphragm 46 can be measured by the pressure sensor 44, with the pressure sensor 44 being a resistive or capacitive sensor, for example a MEMS sensor or MEMS pressure die. In one configuration, the pressure sensor 44 may be that which is marketed and sold under the name NovaSensor®. In an alternative configuration, the pressure sensor 44 may be a silicon, micro-machined, piezo resistive pressure sensing chip within the Smi510E Series. In other configurations, the pressure sensor 44 may be another type of sensor configured to measure hydraulic pressure.

Figure 3:
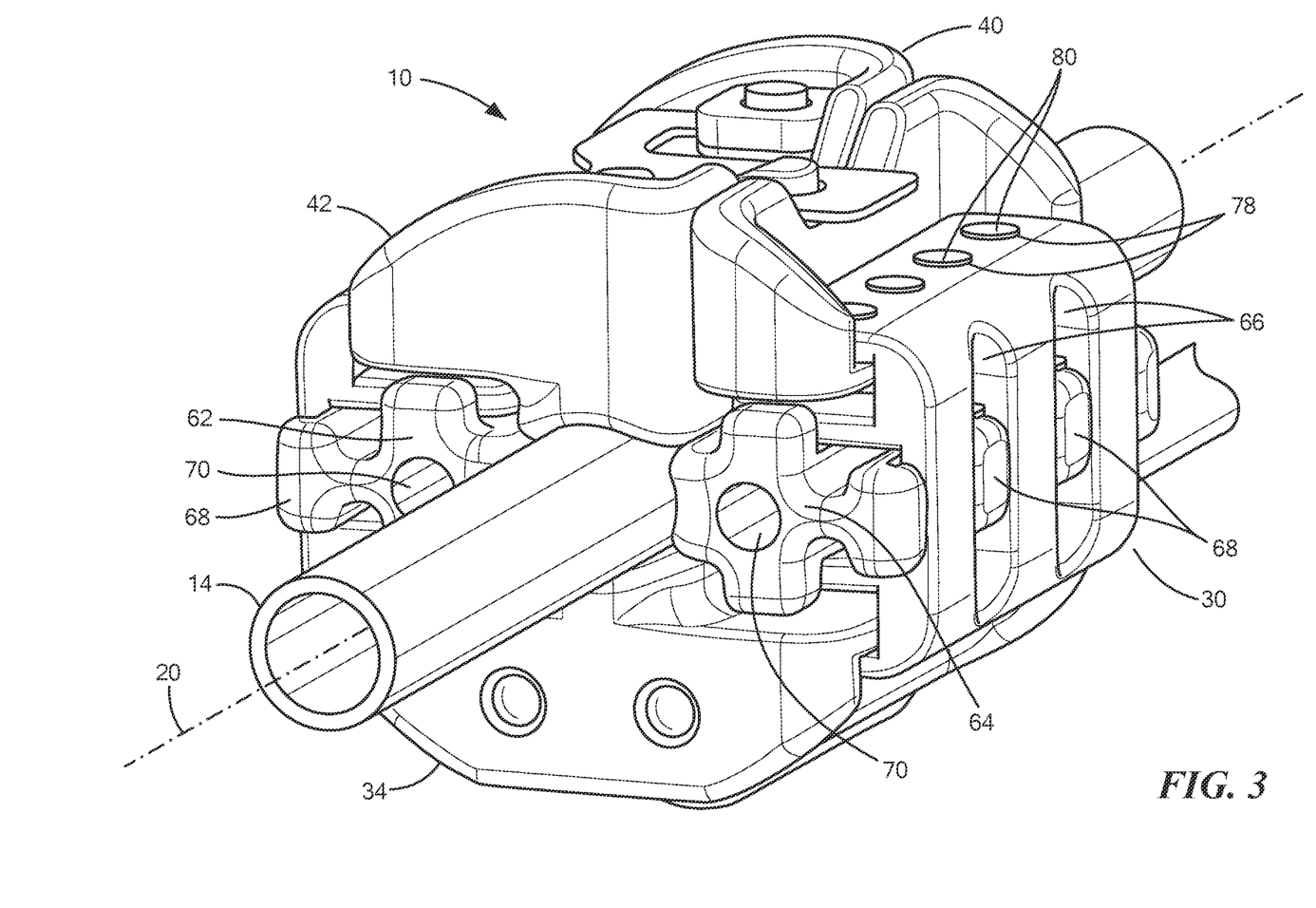
FIG. 3 is a front perspective view of the cuff shown n FIG. 1 with a mock artery disposed within the cuff.
Figure 4:
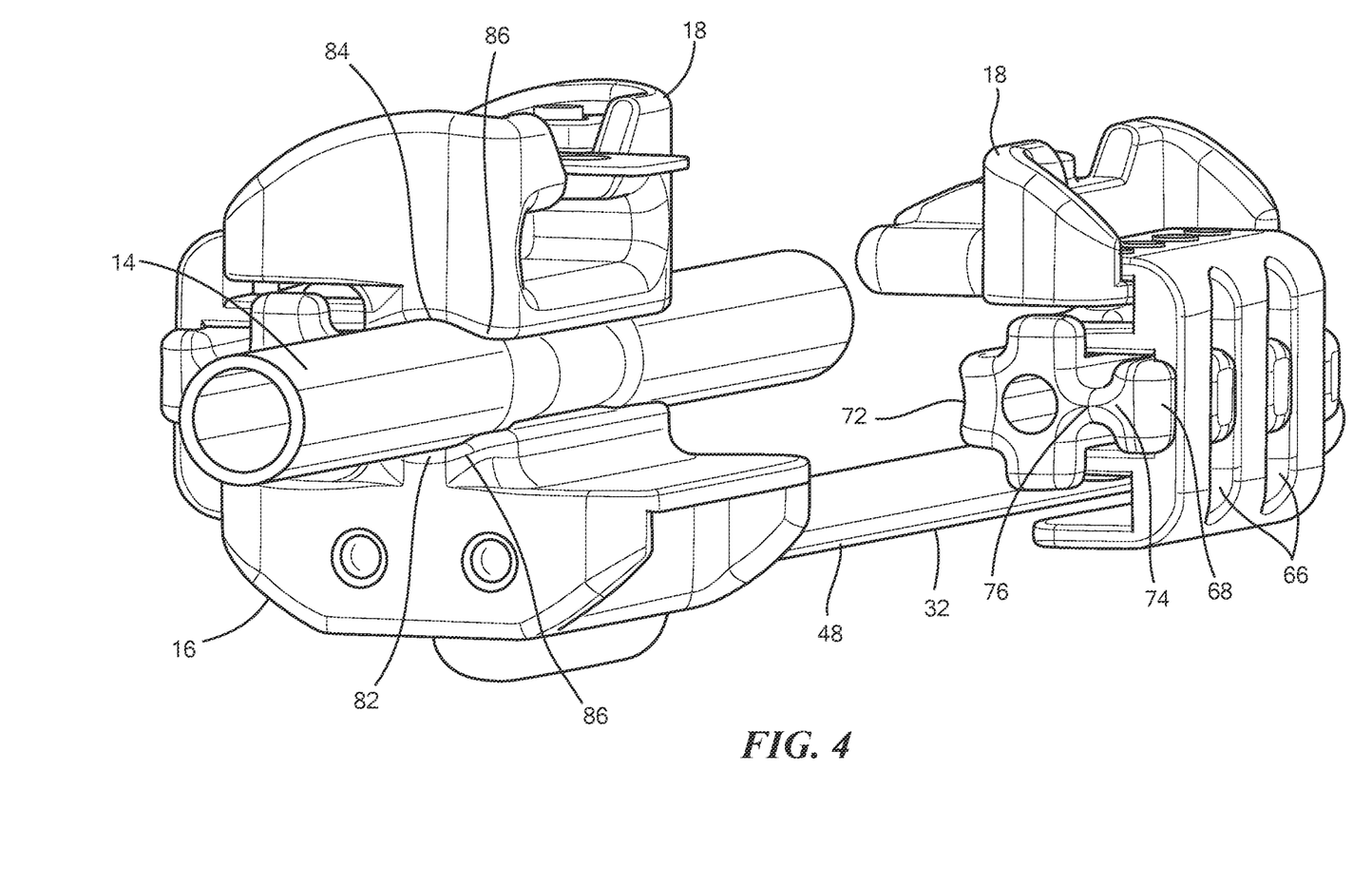
FIG. 4 is a partially disassembled view of the cuff shown in FIG. 3.
Figure 5:
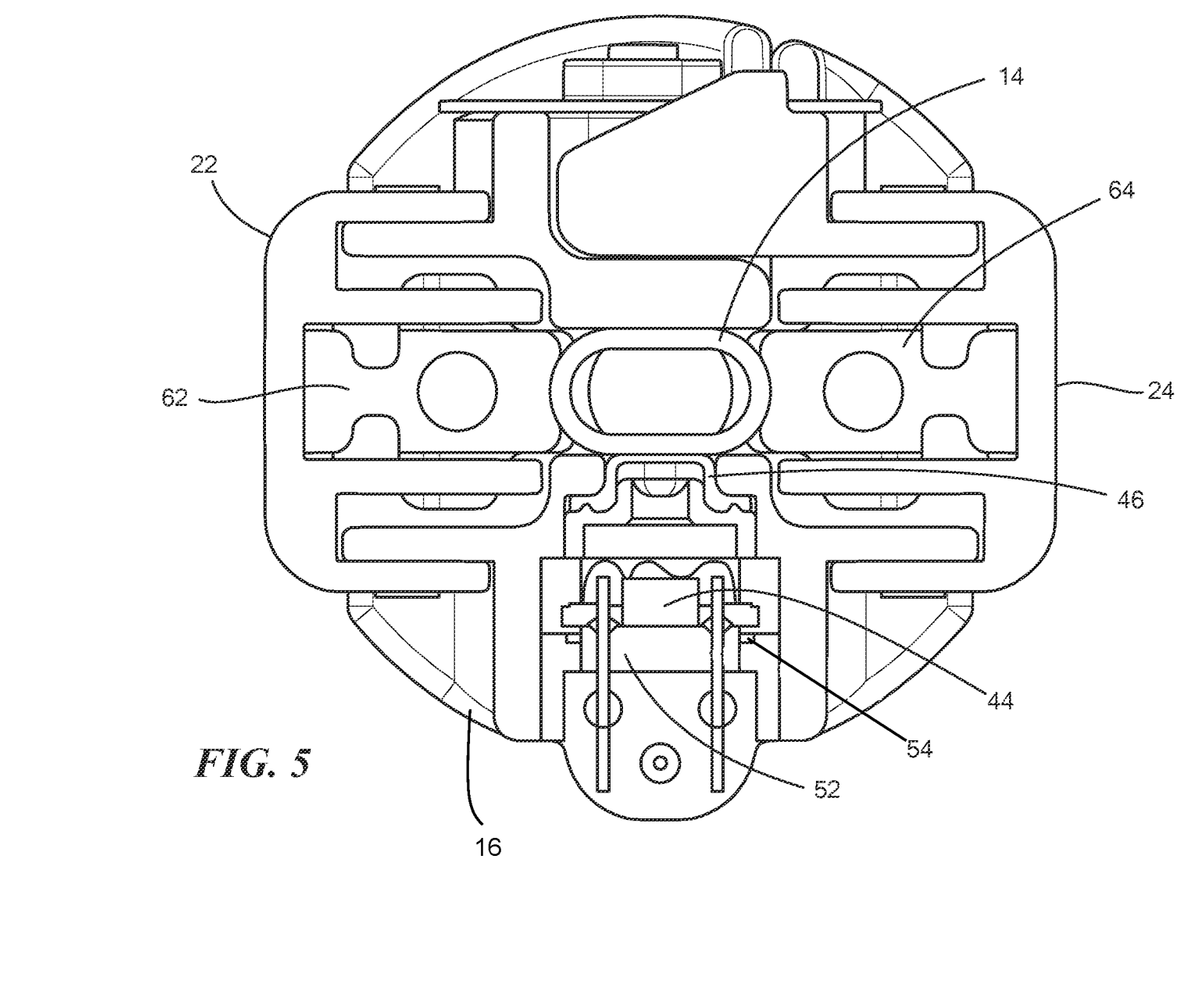
FIG. 5 is an axial sectional view of the cuff shown in FIG. 3 at the mid-plane.
Figure 6:
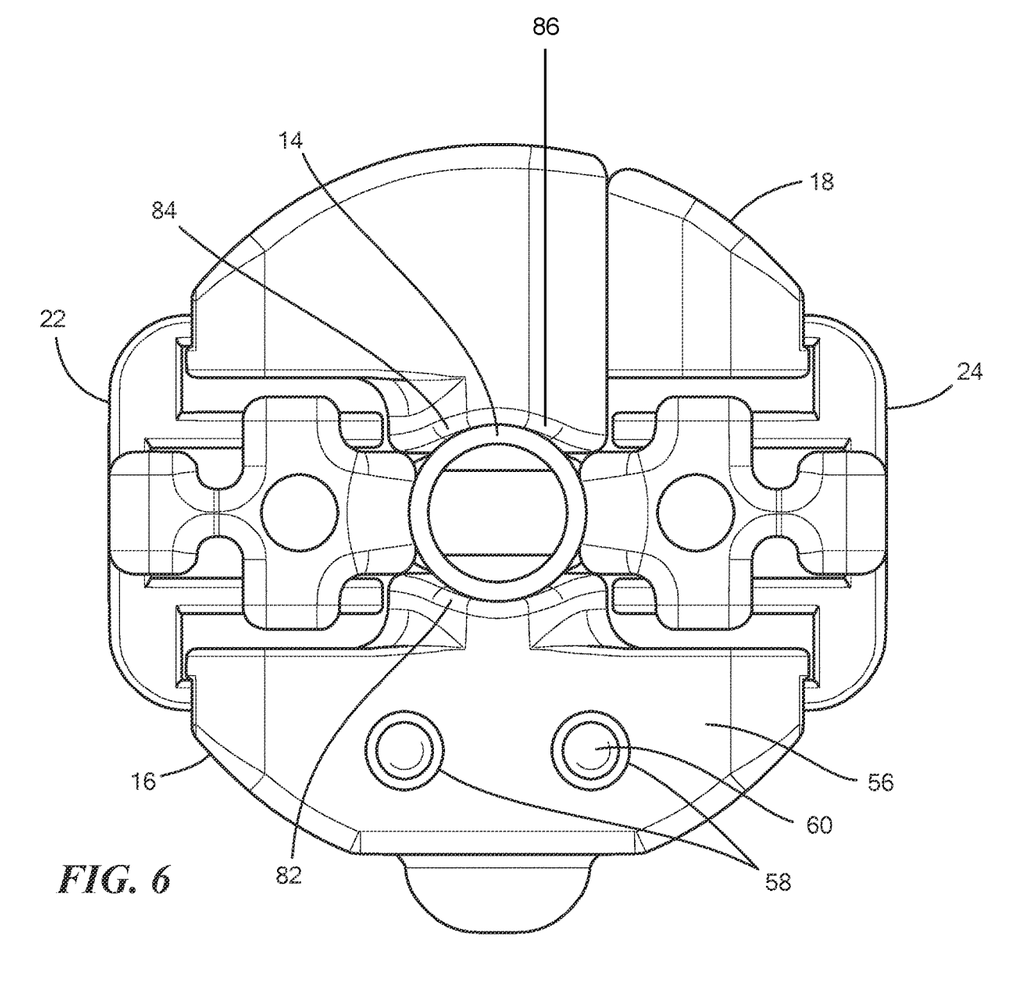

As shown in FIGS. 1-4 and 6, in order to insert the fluid within the fluid chamber 52, the housing 26 of the first brace portion 16 includes a sidewall 56 defining one or more ports 58, for example a fill port and a vent port, in fluid communication with the fluid chamber 52 (as shown in FIG. 5). The fill port may be used to deposit and adjust the amount of the fluid, e.g., silicone, located within the fluid chamber 52, whereas the vent portion may be used to receive a vacuum to remove any entrapped air from the fluid chamber 52. The removal of air assists in providing the fluid that is free of air bubbles in an effort to obtain accurate hydraulic pressure measurements. As shown in FIGS. 3-4 and 6, a stopper 60, for example a ceramic ball, may be disposed within each of the ports 58 to provide a hermetic seal.

Figure 7:
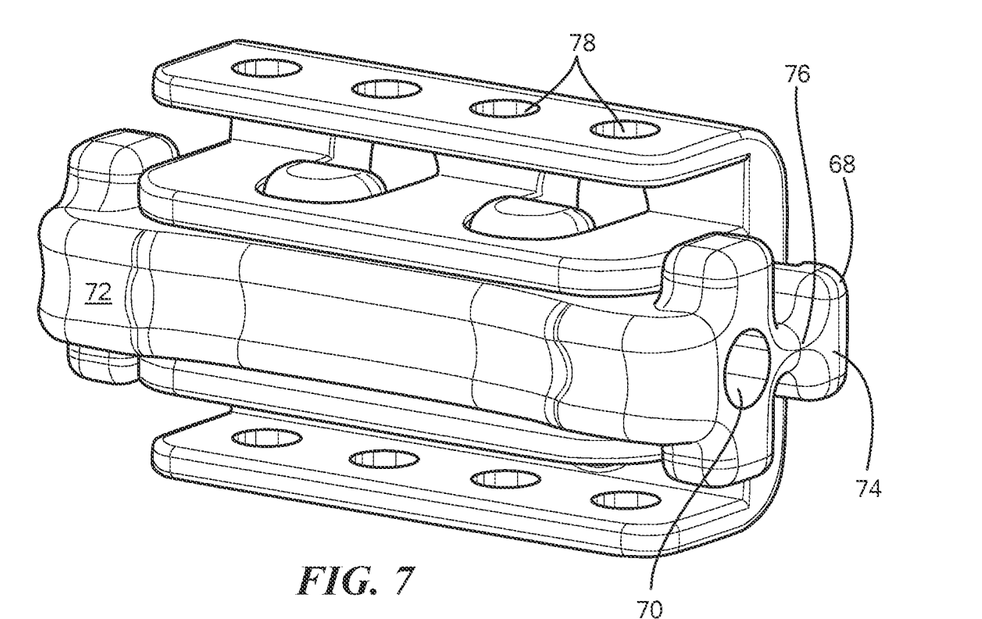
FIG. 7 is a side perspective view of the lateral restraint shown in FIG. 1 facing the blood vessel receiving volume of the cuff.
Figure 8:
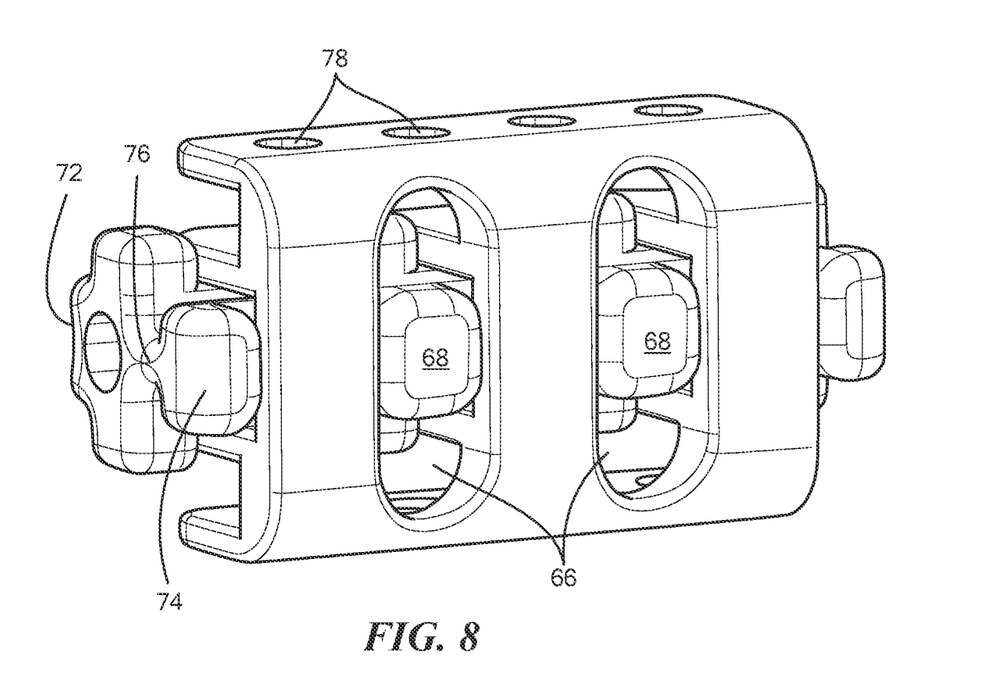
FIG. 8 is a side perspective view of the lateral restraint shown in FIG. 1 facing away from the blood vessel receiving portion of the cuff.

Now referring to FIGS. 6-8, disposed between the first brace portion 16 and the second brace portion 18 are a first lateral restraint 62 and a second lateral restraint 64 separated from each by a blood vessel receiving volume defined by the first lateral restraint 62, the second lateral restraint 64, and the first and second brace portions 16, 18. That is, the first and second lateral restraints 62, 64 are symmetric around the blood vessel when the blood vessel is received within the cuff 12 and contour the blood vessel 14. The first restraint 62 and the second restraint 64 are configured to allow the blood vessel to pulsate when received with the cuff 12. In particular, the first restraint 62 and the second restraint 64 may be pliable, for example, by being composed of silicone or other similar low durometer material. As described herein, the first bracket 22 and the second bracket 24 are included with the cuff 12 and are disposed on opposite sides of the pressure sensor 44 and are configured to affix the first brace portion 16 to the second brace portion 18 and to maintain the first brace portion 16 and the second brace portion 18 at a fixed distance. The first lateral restraint 62 is at least partially disposed within the first bracket 22 and the second lateral restraint 64 is at least partially disposed with the second bracket 24. For example, the first and second brackets 22, 24 include apertures 66 sized and configured to receive corresponding protuberances 68 on the restraints 62, 64 which extend out through the apertures 66 in a direction orthogonal to the longitudinal axis 20 between the brace portions 16, 18. Such a configuration allows for the restraints 62, 64 to be displaced during blood vessel pulsation in a direction orthogonal to the longitudinal axis 20 between the brace portions 16, 18 and return to their original position following blood vessel pulsation.

Each restraint 62, 64 further includes a bore 70 extending therethrough and voids that allow for flexion of the restraint. For example, each restraint 62, 64 may include a first portion 72 configured to contour and being in contact with a blood vessel, for example, an artery, and a second portion 74 configured to extend through the apertures 66 of the brackets 22, 24. The first portion 72 and the second portion 74 are connected to each other by a necked portion 76 of smaller thickness than the first portion 72 and/or the second portion 74. This reduction in thickness creates a displacement volume or void between the first portion 72 and the second portion 74 which allows compliance of the restraints 62, 64. The first portion 72 of each restraint 62, 64 is also configured to extend into apertures 66 that are aligned by with the longitudinal axis 20.

Further, the first and second brackets 22, 24 define one or more openings 78 each sized to receive at least one protrusion 80 coupled to each housing 26, 36. The receiving of the protrusions 80 through the openings 78 facilitates the coupling of the first and second brackets 22, 24 to the housings 26, 36.

As shown in FIG. 6, the fixation of the first brace portion 16 and the second brace portion 18 by the first and second brackets 22, 24 allows an abutment structure 82, i.e., inner wall, of the first brace portion 16 and an abutment structure 84 of the second brace portion 18 to move with respect to each other when at least partially surrounding the blood vessel 12. In particular, the abutment structures 82 and 84 each define a blood vessel securing region 86 sized and shaped to receive the blood vessel 14 therein. The abutment structure 84 of the second brace portion 18 may include the same or similar features as the abutment structure 82 of the first brace portion 16.

Although not shown in the referenced drawings for simplicity, the blood vessel securing region 86 includes one or more curved regions, such as a pair of curved or rounded edges, one or more cylindrical support surfaces (not shown), and one or more transition regions (not shown) adapted for contact with the blood vessel wall. The securing region 86 may have sufficient depth and curvature to maintain long-term alignment of the housing axis with an axis of the blood vessel 12 to prevent misalignment due to rotational movement and/or forces that would cause the sensor tilt or displace in a direction perpendicular to the artery axis. The rounded edges define a perimeter around each respective abutment structure 82, 84. The cylindrical support surface is disposed between the rounded edges at one or both ends of the abutment structures 82 along the housing axis.

When the cuff 12 is used as a blood pressure sensor, the blood vessel securing region 86 is adapted to minimize stress imposed on the blood vessel 12 in undergoing a forced transition from a circular geometry to a constrained flattening of the blood vessel (as shown in FIG. 5) for achieving applanation and accurate blood pressure transduction through the blood vessel wall to the diaphragm 46. The design of the abutment structure 82 allows the cuff 12 to least partially surround the blood vessel 14 without overly constraining the blood vessel 14 when obtaining the blood pressure measurements or performing alternative medical diagnostics.

It will be appreciated by persons skilled in the art that the present embodiments are not limited to what has been particularly shown and described herein above. In addition, unless mention was made above to the contrary, it should be noted that all of the accompanying drawings are not to scale. A variety of modifications and variations are possible in light of the above teachings.

What is claimed is:

1. An implantable extravascular pressure sensing system, comprising:
a cuff including a first brace portion affixed to a second brace portion and defining a longitudinal axis therebetween, the first brace portion defining a fluid chamber, the fluid chamber defining a recessed aperture;

a first lateral restraint and a second lateral restraint each defining a bore there through and being disposed between the first brace portion and the second brace portion, the first lateral restraint and the second lateral restraint being configured to be displaceable in a direction orthogonal to the longitudinal axis;

a diaphragm coupled to the fluid chamber and sealing the recessed aperture;

a fluid disposed within the fluid chamber for exhibiting a hydraulic pressure in communication with the diaphragm; and a pressure sensor coupled to the first brace portion, the pressure sensor being configured to measure a change in the hydraulic pressure when a force is imparted on the diaphragm.

2. The system of claim 1, further including a first bracket and a second bracket, the first bracket and the second bracket being disposed on opposite sides of the pressure sensor and configured to affix the first brace portion to the second brace portion.

3. The system of claim 2, wherein the first lateral restraint is at least partially disposed within the first bracket and the second lateral restraint is at least partially disposed within the second bracket.

4. The system of claim 3, wherein the first bracket and the second bracket each include a first plurality of apertures, and wherein the first lateral restraint and the second lateral restraint each include a first plurality of protuberances sized and configured to be displaceable into and out of the first plurality of apertures.

5. The system of claim 4, wherein the first plurality of protuberances extends away from each of a respective one of the first lateral restraint and the second lateral restraint in a direction orthogonal to the longitudinal axis.

6. The system of claim 1, wherein the first lateral restraint and the second lateral restraint are pliable.

7. The system of claim 1, wherein the first lateral restraint and the second lateral restraint are configured to contour a blood vessel restrained between them.

8. The system of claim 1, wherein the first lateral restraint and the second lateral restraint each include a blood vessel contact portion and a first plurality of protuberances spaced a distance from the blood vessel contact portion.

9. The system of claim 8, wherein the first plurality of protuberances are separated from the blood vessel contact portion by a necked portion.

10. An implantable extravascular pressure sensing system, comprising:

a cuff including a first brace portion affixed to a second brace portion at a fixed distance and defining a longitudinal axis and a blood vessel receiving volume therebetween, the first brace portion defining a fluid chamber, the fluid chamber defining a recessed aperture;

a first lateral restraint and a second lateral restraint disposed between the first brace portion and the second brace portion, the first lateral restraint and the second lateral restraint each defining a bore there through and being pliable and configured to be displaceable in a direction orthogonal to the longitudinal axis and to substantially enclose the blood vessel receiving volume;

a diaphragm coupled to the fluid chamber and sealing the recessed aperture;

a fluid disposed within the fluid chamber for exhibiting a hydraulic pressure in communication with the diaphragm; and a pressure sensor coupled to the first brace portion, the pressure sensor being configured to measure a change in the hydraulic pressure when a force is imparted on the diaphragm.

11. The system of claim 10, further including a first bracket and a second bracket, the first bracket and the second bracket being disposed on opposite sides of the pressure sensor and configured to affix the first brace portion to the second brace portion.

12. The system of claim 11, wherein the first lateral restraint is at least partially disposed within the first bracket and the second lateral restraint is at least partially disposed within the second bracket.

13. The system of claim 12, wherein the first bracket and the second bracket each include a first plurality of apertures, and wherein the first lateral restraint and the second lateral restraint each include a first plurality of protuberances sized and configured to be displaceable into and out of the first plurality of apertures.

14. The system of claim 13, wherein the first plurality of protuberances extends away from each of a respective one of the first lateral restraint and the second lateral restraint in a direction orthogonal to the longitudinal axis.

15. The system of claim 10, wherein the first lateral restraint and the second lateral restraint are at least partially composed of silicone.

16. The system of claim 10, wherein the first lateral restraint and the second lateral restraint each include a blood vessel contact portion and a first plurality of protuberances spaced a distance from the blood vessel contact portion.

17. The system of claim 16, wherein the first plurality of protuberances are separated from the blood vessel contact portion by a necked portion.

18. An implantable extravascular pressure sensing system, comprising:

a cuff including a first brace portion affixed to a second brace portion and defining a longitudinal axis and a blood vessel receiving volume therebetween, the first brace portion defining a fluid chamber, the fluid chamber defining a recessed aperture;

a first lateral restraint and a second lateral restraint disposed between the first brace portion and the second brace portion, the first lateral restraint and the second lateral restraint being pliable and being configured to be displaceable in a direction orthogonal to the longitudinal axis and to substantially enclose the blood vessel receiving volume;

a first bracket and a second bracket, the first bracket and the second bracket being disposed on opposite sides of a pressure sensor and configured to affix the first brace portion to the second brace portion;

the first lateral restraint and the second lateral restraint each including:
  a first portion configured to contact a blood vessel when a blood vessel is disposed within the blood vessel receiving volume;
  a second portion spaced a distance from the first portion by a necked portion, the second portion being configured to move within a portion of a respective one of the first bracket and the second bracket; and
  a bore extending through the first portion;

a diaphragm coupled to the fluid chamber and sealing the recessed aperture;

a fluid disposed within the fluid chamber for exhibiting a hydraulic pressure in communication with the diaphragm; and the pressure sensor coupled to the first brace portion, the pressure sensor being configured to measure a change in the hydraulic pressure when a force is imparted on the diaphragm.

\* \* \* \* \*